US006190345B1

(12) United States Patent
Henderson

(10) Patent No.: US 6,190,345 B1
(45) Date of Patent: Feb. 20, 2001

(54) VERTEBRAL TRACTION DEVICE AND METHOD

(76) Inventor: Joseph E. Henderson, 5422 Spahn Ave., Lakewood, CA (US) 90713

( * ) Notice: Under 35 U.S.C. 154(b), the term of this patent shall be extended for 0 days.

(21) Appl. No.: 09/492,421

(22) Filed: Jan. 27, 2000

Related U.S. Application Data

(60) Provisional application No. 60/162,507, filed on Oct. 29, 1999, and provisional application No. 60/159,079, filed on Oct. 12, 1999.

(51) Int. Cl.7 ..................................................... A61F 15/00

(52) U.S. Cl. ................................. 602/32; 602/33; 602/35

(58) Field of Search ............................ 602/32–36, 38–40; 606/241, 242; 482/121, 124, 129, 130

(56) References Cited

U.S. PATENT DOCUMENTS

| | | | | |
|---|---|---|---|---|
| 2,940,441 | * | 6/1960 | Demarest | 602/32 |
| 2,940,442 | * | 6/1960 | Wilhelm | 602/32 |
| 4,002,165 | | 1/1977 | Lind | 128/71 |
| 4,026,548 | * | 5/1977 | Birdwell | 482/129 |
| 4,073,290 | | 2/1978 | Farrar, Jr. | 128/75 |
| 4,356,816 | * | 11/1982 | Granberg | 606/241 X |
| 4,407,274 | * | 10/1983 | Goodley | 606/241 |
| 4,538,598 | * | 9/1985 | Gill | 602/33 |
| 4,582,319 | * | 4/1986 | Luna | 482/130 |
| 4,627,423 | | 12/1986 | Kampner | 128/75 |
| 4,664,099 | | 5/1987 | Pearl, Jr. | 128/75 |
| 4,674,484 | | 6/1987 | Kott | 128/75 |
| 4,865,022 | | 9/1989 | Gorsen | 128/75 |
| 4,930,524 | | 6/1990 | van Zuilichem | 128/876 |
| 4,995,378 | * | 2/1991 | Dyer | 606/241 |
| 5,234,392 | * | 8/1993 | Clark | 482/130 X |
| 5,258,017 | | 11/1993 | Myers et al. | 606/241 |
| 5,303,716 | * | 4/1994 | Mason | 482/148 X |
| 5,306,231 | | 4/1994 | Cullum et al. | 602/32 |
| 5,306,232 | * | 4/1994 | Whitmyer | 602/32 |
| 5,370,605 | | 12/1994 | Weed | 602/35 |
| 5,401,236 | | 3/1995 | Summerville | 602/33 |
| 5,494,048 | * | 2/1996 | Carden | 602/32 X |
| 5,772,622 | | 6/1998 | Friske | 602/36 |

FOREIGN PATENT DOCUMENTS

| | | | | |
|---|---|---|---|---|
| 810930 | * | 4/1969 | (CA) | 602/33 |

* cited by examiner

*Primary Examiner*—Mickey Yu
*Assistant Examiner*—Denise Pothier
(74) *Attorney, Agent, or Firm*—David A. Farah; Sheldon & Mak

(57) ABSTRACT

A vertebral traction device for applying traction to the lower vertebral column. A method for applying traction to the lower vertebral column.

25 Claims, 7 Drawing Sheets

VERTEBRAL TRACTION DEVICE AND METHOD

CROSS-REFERENCE TO RELATED APPLICATIONS

The present application is a Continuation-in-Part of United States Provisional Patent Application No. 60/162,507, entitled "A Traction Device to Apply Tension to the Spine for Use in a Bed" filed Oct. 29, 1999; and also a Continuation-in-Part of United States Provisional Patent Application No. 60/159,079, entitled "Traction Device to Apply Tension to the Spine for Use in a Bed" filed Oct. 12, 1999, the contents of which are incorporated herein by reference in their entirety.

BACKGROUND

Diseases and injuries of the lower back are a common cause of morbidity. Treatment for diseases and injuries of the lower back, particularly for ruptured vertebral disks, includes rest, physical therapy, pharmacotherapy and surgery. Another common treatment is the application of traction to distract the vertebrae adjacent to the ruptured disk to relieve pressure created by the ruptured disk material.

A myriad of devices has been developed to apply traction to a patient's lower vertebral column. Disadvantageously, however, most of these devices are either complex or cumbersome, or require trained healthcare personnel to place the device on the patient. Further, most traction devices tend to be uncomfortable to use overnight as they restrict natural movement during sleep.

Therefore, there remains a need for a device for applying traction to the lower vertebral column which does not require trained healthcare personnel to place on and to remove. Further, there remains a need for a device for applying traction to the lower vertebral column which can be worn comfortably while sleeping.

SUMMARY

According to one embodiment of the present invention, there is provided a vertebral traction device for applying traction to the lower vertebral column. The device comprises a support having a top end, a bottom end, a front side and a back side. The device further comprises a bed attachment cable having a proximal end and a distal end, where the proximal end of the bed attachment cable is attached to the support at or near the bottom end of the support. The device also comprise a tension provider having a proximal end and a distal end, where the proximal end of the tension provider is attached to the support. The device further comprises a harness attachment cable having a proximal end and a distal end, where the proximal end of the harness attachment cable is attached to the tension provider at or near the distal end of the tension provider, where the distal end of the harness attachment cable has a long axis. The device also comprises a harness comprising a belt and a belt attachment cable, where the belt attachment cable has a first end and a second end, and where the first end and the second end are connected to the belt. The device further comprises a belt attachment cable connector slidably attached to the belt attachment cable; and a swivel connected to the belt attachment cable connector and to the harness attachment cable. The swivel allows the harness to rotate freely about the long axis of the distal end of the harness attachment cable.

In a preferred embodiment, the support comprises a board structure. In another preferred embodiment, the support comprises a foot member attached at or near the bottom end of the support. In a particularly preferred embodiment, the support comprises an enclosure connected to the back side for enclosing the tension provider. In another preferred embodiment, the distal end of the bed attachment cable comprises a clip for reversibly attaching the distal end of the bed attachment cable to the bed attachment cable at a point proximal to the distal end of the bed attachment cable.

In another preferred embodiment, the tension provider is a spring. Further, the device can comprise a harness attachment cable connector, where the swivel is connected to the harness attachment cable by the harness attachment cable connector.

In a particularly preferred embodiment, the belt attachment cable connector is attached to the belt attachment cable by a pulley.

According to another embodiment of the present invention, there is provided a method for applying traction to the lower vertebral column of a patient reclining on a bed. The method comprises, first, providing a device according to the present invention. Then, the bed attachment cable is attached to the frame of the bed and the waist of the patient is encircled by the belt such that the belt attachment cable is between the patient's legs. Further, the belt attachment cable is connected to the harness attachment cable connector through the swivel; and the patient is positioned on the bed at a distance from the top end of the support to cause the tension provider to stretch, thereby transmitting tension through the harness attachment cable and harness, and thereby placing traction on the lower vertebral column.

In a preferred embodiment, connecting the belt attachment cable to the harness attachment cable connector through the swivel further comprises attaching the swivel to a harness attachment cable connector connected to the harness attachment cable.

According to another embodiment of the present invention, there is provided a method for applying traction to the lower vertebral column of a patient reclining on a bed. The method comprises placing a harness around a patient's waist where the harness is connected to a swivel and where placing the harness results in the swivel being between the patient's legs. Then, the swivel is attached to a tension provider at the foot of the bed; and tension is allowed to transmit from the tension provider through the swivel between the patient's legs to the harness, thereby causing traction to the lower vertebral column of the patient.

According to another embodiment of the present invention, there is provided a vertebral traction device for applying traction to the lower vertebral column. The device comprises a support having a top end, a bottom end, a front side and a back side. The device further comprise a bed attachment cable having a proximal end and a distal end, where the proximal end of the bed attachment cable is attached to the support at or near the bottom end of the support. The device also comprises a tension provider having a proximal end and a distal end, where the proximal end of the tension provider is attached to the support. The device further comprises a harness attachment cable having a proximal end and a distal end, where the proximal end of the harness attachment cable is attached to the tension provider at or near the distal end of the tension provider, where the distal end of the harness attachment cable passes from the back side of the support to the front side of the support, and where the distal end of the harness attachment cable has a long axis. The device also comprises a harness comprising a belt and a belt attachment cable, where the belt attachment cable has a first end and a second end, and where the first end and the second end are connected to the belt; and a belt attachment cable connector slidably attached to the belt attachment cable by a pulley.

In a preferred embodiment, the support comprises a board structure. In another preferred embodiment, the support comprises a foot member attached at or near the bottom end of the support. In yet another preferred embodiment, the support comprises an enclosure connected to the back side for enclosing the tension provider.

In another preferred embodiment, the distal end of the bed attachment cable comprises a clip for reversibly attaching the distal end of the bed attachment cable to the bed attachment cable at a point proximal to the distal end of the bed attachment cable. In yet another preferred embodiment, the tension provider is a spring.

In a particularly preferred embodiment, the device additionally comprises a swivel connected to the belt attachment cable connector and to the harness attachment cable, where the swivel allows the harness to rotate freely about the long axis of the distal end of the harness attachment cable. In another particularly preferred embodiment, the device additionally comprises a harness attachment cable connector, where the swivel is connected to the harness attachment cable by the harness attachment cable connector.

According to one embodiment of the present invention, there is provided a method for applying traction to the lower vertebral column of a patient reclining on a bed. The method comprises providing a device according to the present invention. Then, the bed attachment cable is attached to the frame of the bed. Then, the waist of the patient is encircle by the belt such that the belt attachment cable is between the patient's legs. Next, the belt attachment cable is connected to the harness attachment cable connector; and the patient is positioned on the bed at a distance from the top end of the support to cause the tension provider to stretch, thereby transmitting tension through the harness attachment cable and harness, and thereby placing traction on the lower vertebral column.

According to one embodiment of the present invention, there is provided a method for applying traction to the lower vertebral column of a patient reclining on a bed. The method comprises placing a harness around a patient's waist where the harness is connected to a pulley. Then, the pulley is attached to a tension provider at the foot of the bed; and the tension is allowed to transmit from the tension provider through the pulley between the patient's legs to the harness, thereby causing traction to the lower vertebral column of the patient.

FIGURES

The features, aspects and advantages of the present invention will become better understood with regard to the following description, appended claims and accompanying figures where:

DESCRIPTION

In one embodiment, the present invention is a vertebral traction device for applying traction to the lower vertebral column. The device is simple to put on and to remove and does not require trained healthcare personnel to supervise daily usage if the patient using the device has a moderate level of dexterity. Further, the device can be worn comfortably while sleeping.

In another embodiment, the present invention is a method for applying traction to the lower vertebral column. The method comprises donning a vertebral traction device according to the present invention, and allowing the device to apply traction to the lower vertebral column. The device and method will now be described in more detail.

Figure 1:
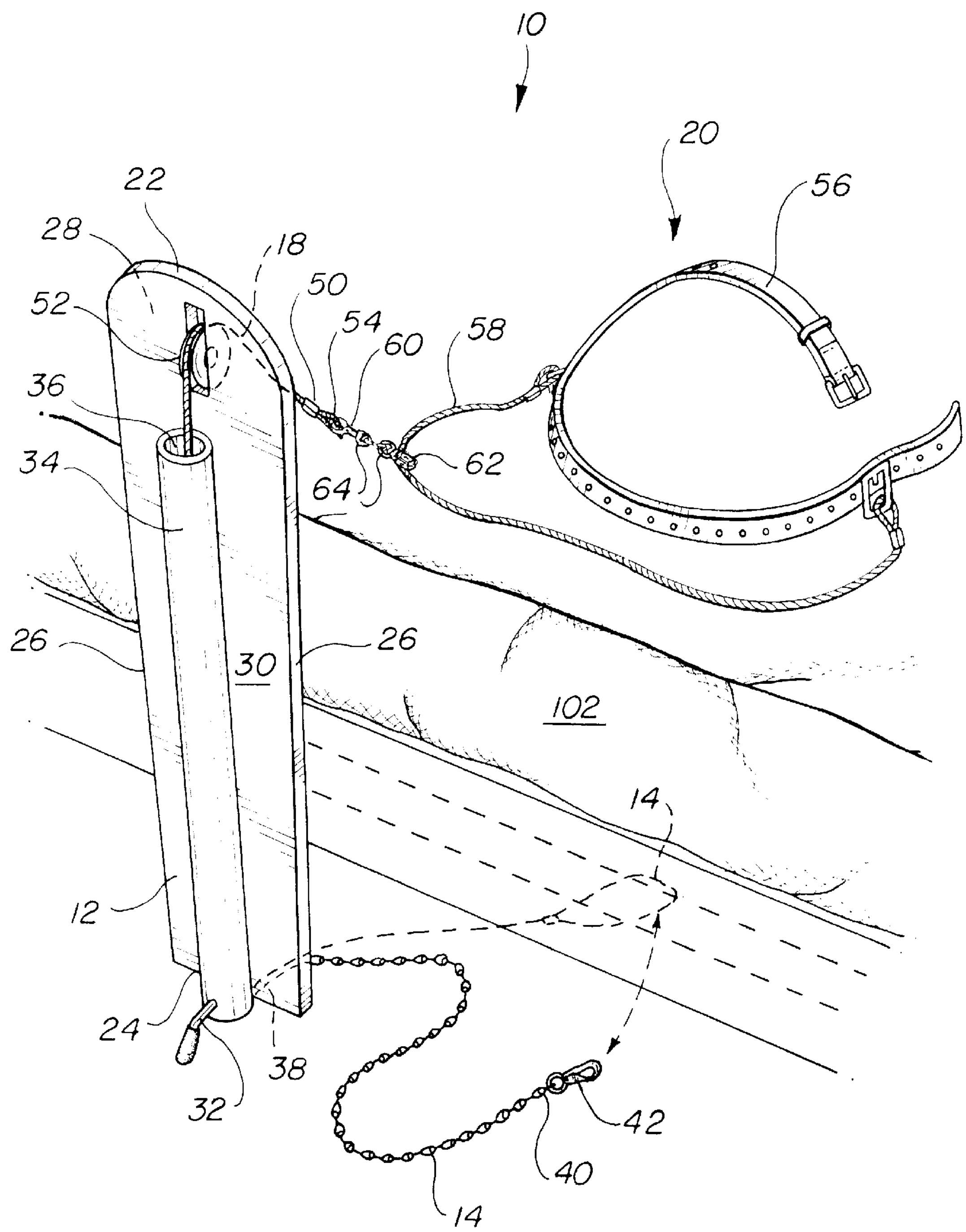
FIG. 1 is a side perspective view of one embodiment of the vertebral traction device according to the present invention.
Figure 2:
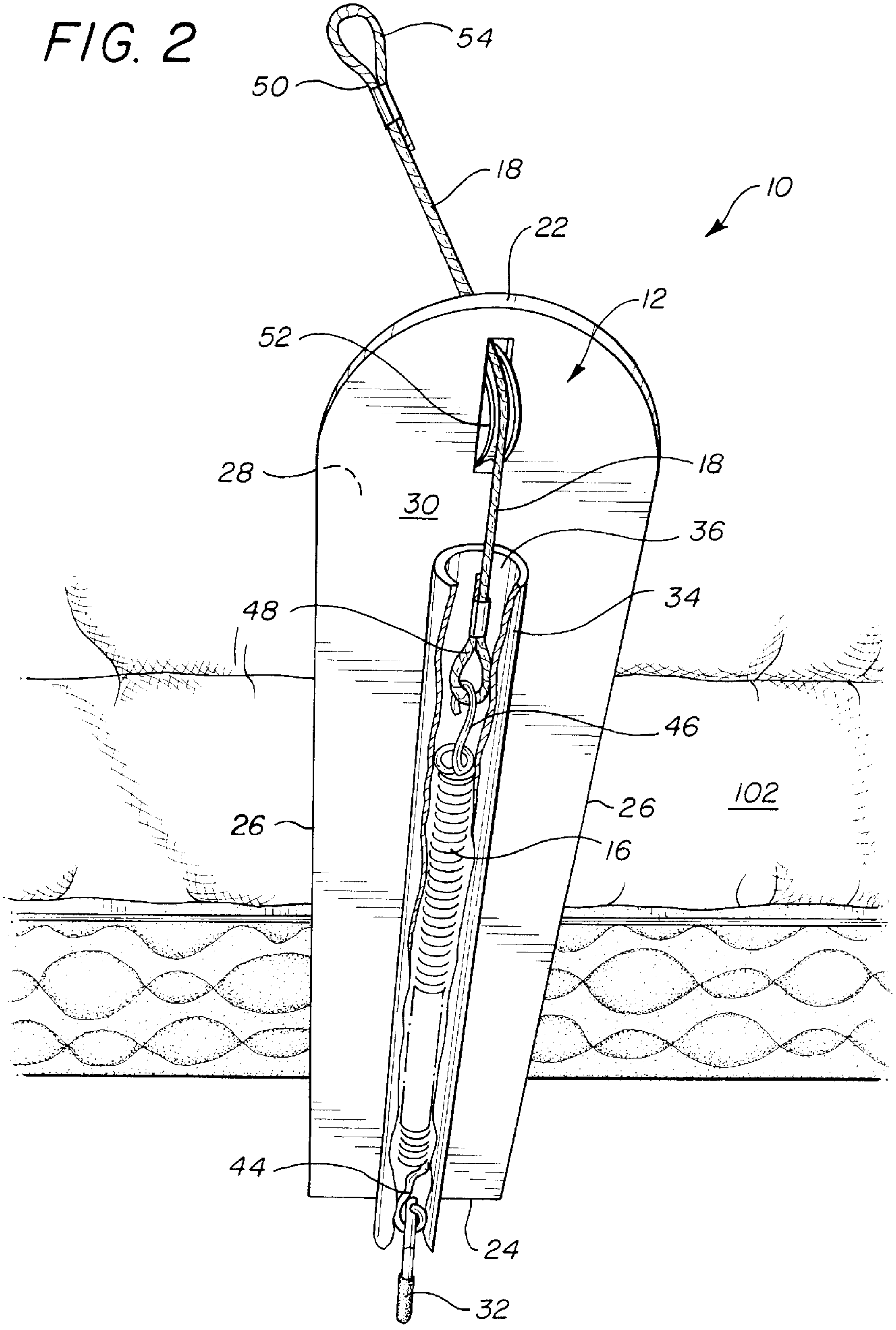
FIG. 2 is a back perspective, partial cutaway view of the device shown in FIG. 1.

The vertebral traction device for applying traction to the lower vertebral column according to the present invention comprises generally several interconnecting parts. Referring now to FIGS. 1 and 2, there is shown a side perspective view and a back perspective, partial cutaway view of the device 10, which comprises a support 12, a bed attachment cable 14, a tension provider 16, a harness attachment cable 18 and a harness 20. The support 12 is designed to rest firmly against the foot end of a mattress and box spring combination of a conventional bed. The support 12 can be a board structure as shown, or can be a rod or other stiff member. A support 12 having a board structure is preferred as the board structure lends stability to the device 10 without tending to indent or otherwise damage the mattress or box spring during use of the device 10.

The support 12 has a top end 22, a bottom end 24, two lateral sides 26, a front side 28 and a back side 30. The top end 22 is preferably rounded and smooth so that is does not damage sheets or bed coverings, or injure the patient during use. The bottom end 24 is preferably flat to rest evenly on the floor.

In a preferred embodiment, the support 12 includes a foot member 32 attached at or near the bottom end 24 of the support 12. The foot member 32 increases the stability of the device 10 by allowing the support 12 to stand upright, countering the tendency for the top end 22 to fall away from the mattress and box spring when traction is not being applied to the patient's lower vertebral column.

The front side 28 of the support 12 that will contact the mattress and box spring combination during use is preferably smooth to provide even pressure against the mattress and box spring during use. The back side 30 preferably comprises an enclosure 34 having an open top end 36 for enclosing most or all of the tension provider 16 so that the tension provider 16 does not damage sheets or bed coverings, or injure the patient during use.

The support 12 can be made of wood, metal, plastic or other natural or synthetic material that is sufficiently stiff to transmit tension from the bed attachment cable 14 through the tension provider 16 to the harness 20. Preferably, the support 12 is made of inexpensive, light weight material which is easy to manufacture into the proper shape and which will withstand the forces generated during use of the device 10.

The device 10 further includes a bed attachment cable 14 having a proximal end 38 and a distal end 40. The proximal end 38 is attached to the support 12 at or near the bottom end 24. In a preferred embodiment, the proximal end 38 is reversibly attached to allow easy disassembly for storage and shipping.

The bed attachment cable 14 functions to reversibly connect the support 12 to the bed frame. This function can be accomplished in several ways. For example, the distal end 40 can be tied directly to the bed frame underneath the box spring. Alternately, the distal end 40 of the bed attachment cable 14 is brought around the bed frame underneath the box spring and can be attached directly to the support, such as by having a hook at the distal end 40 interface with a ring on the support 12. In a preferred embodiment, this function is accomplished by having the distal end 40 of the bed attachment cable 14 brought around the bed frame underneath the box spring and then connecting the distal end 40 directly to the bed attachment cable 14 at a point proximal to the distal end by means of a suitable connector.

The bed attachment cable 14 can be made of a variety of natural or synthetic materials such as wire, rope or nylon cord. In a preferred embodiment, the bed attachment cable 14 is made of chain and the distal end 40 includes a clip 42 that can be reversibly attached to the bed attachment cable 14 at a point proximal to the distal end 40 in order to secure the bed attachment cable 14 to the bed frame. This configuration advantageously allows the bed attachment cable 14 to be easily attached to and removed from the bed frame, and to be easily adjusted to the proper tension.

The device 10 further includes a tension provider 16 having a proximal end 44 and a distal end 46. The proximal end 44 of the tension provider 16 is attached to the support 12, preferably at or near the bottom end 24 of the support 12 on the back side 30 of the support 12, either directly or through a connector. However, though less preferred, the proximal end 44 of the tension provider can also be attached at another position on the support. The tension provider 16 can be any suitable resilient member, such as an elastic cord, which tends to return to its original shape upon deformation. In a preferred embodiment, the tension provider 16 is a spring.

The distal end 46 of the tension provider 16 is attached to proximal end 48 of the harness attachment cable 18. The distal end 50 of the harness attachment cable 18 passes through the support 12 from the back side 30 to the front side 28, over a pulley 52 formed in the top end 22 of the support 12. This configuration allows tension generated by the tension provider 16 to be transmitted to the distal end 50 of the harness attachment cable 18. The distal end 50 of the harness attachment cable 18 preferably includes a harness attachment cable connector 54.

The harness attachment cable 18 can be made of a variety of natural or synthetic materials such as wire or rope. In a preferred embodiment, the harness attachment cable 18 is made of nylon cord which allows the harness attachment cable 18 to glide over the pulley smoothly and to allow contact with the patient's lower extremities without injuring them.

Figure 3:
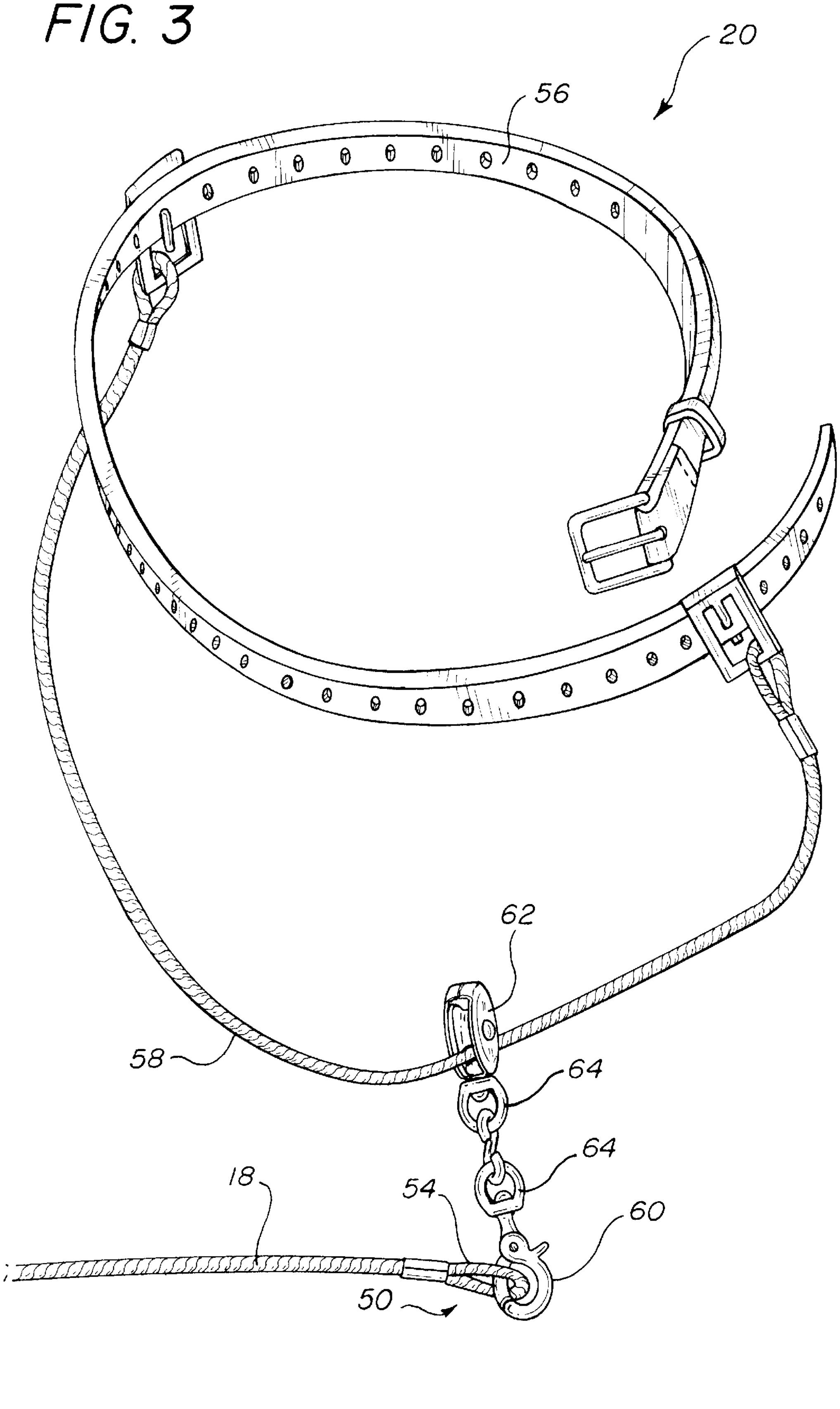
FIG. 3 is a top perspective view of the harness attachment cable and harness portion of the device shown in FIG. 1.

The device 10 also includes a harness 20. Referring now to FIG. 3, there is shown a top perspective view of the harness attachment cable 18 and harness 20 portion of the device 10. The harness 20 comprises a belt 56 and a belt attachment cable 58. The belt 56 is designed to encircle the patient's waist just above the patient's iliac crests. The belt can be made of a variety of natural or synthetic materials such as leather or nylon, and preferably includes a closure member such as a belt buckle which allows the belt to be adjusted to fit comfortably while not slipping toward the patient's lower extremities as traction is applied.

The belt attachment cable 58 has a first end and a second end, and each end is effectively connected to the belt 56 such that, when the belt 56 is fitted to the patient, the two ends are approximately at the front midpoint and back midpoint of the patient's waist. This configuration causes the center portion of the belt attachment cable 58 to rest between the patient's leg when properly fitted.

The device 10 also includes a belt attachment cable connector 60 which is preferably attached to the belt attachment cable 58 by a pulley 62 or other structure or configuration that allows the belt attachment cable connector 60 to slide freely on the belt attachment cable 58. The pulley 62 allows tension to be distributed substantially evenly to both sides of the belt 56 as the patient moves and rotates during use. The belt attachment cable connector 60 is configured to reversibly attach to the distal end 50 of harness attachment cable 18, either directly to the harness attachment cable 18 or to the harness attachment cable connector 54. This attachment allows tension generated by the tension provider 16 and transmitted through the harness attachment cable 18 to be further transmitted to the harness 20.

In a preferred embodiment, the device 10 includes at least one swivel 64 connected to the harness attachment cable 18, or to the harness attachment cable connector 54, when present, and to the belt attachment cable connector 60, which allows the harness 20 to rotate freely about the long axis of the distal end 50 of the harness attachment cable 18. The swivel 64 allows the device 10 to be used comfortably for an extended period while a patient is sleeping by allowing the patient to rotate freely about the long axis of his body while still under traction.

Figure 4:
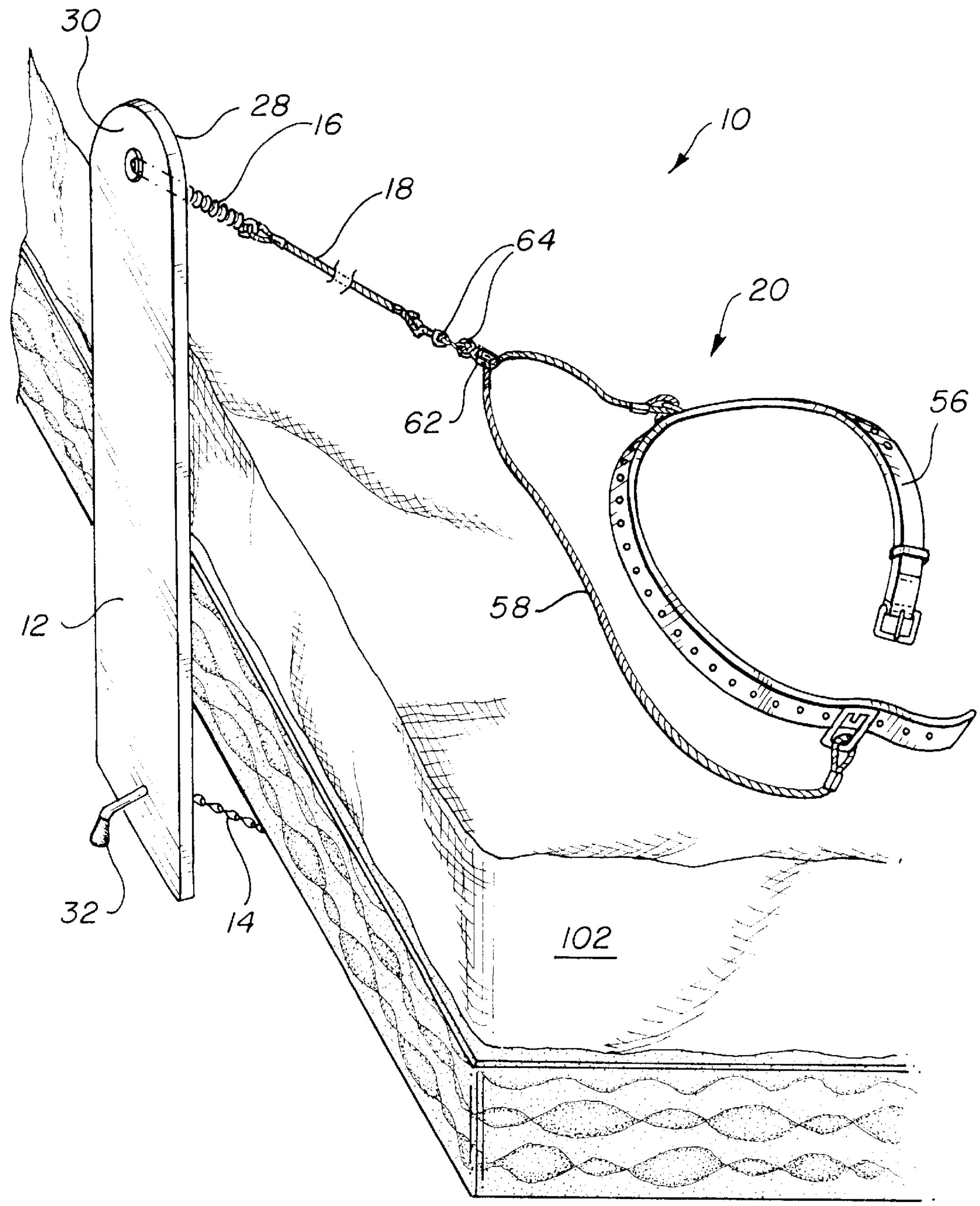
FIG. 4 is side perspective view of another embodiment of the vertebral traction device according to the present invention.

In another preferred embodiment, as shown in FIG. 4, the device 10 comprises a tension provider 16 has a proximal end 44 and a distal end 46. The proximal end is attached to the front side 28 of the support 12 and the distal end is attached to the harness attachment cable 18.

According to another embodiment of the present invention, there is provided a method for applying traction to the lower vertebral column of a patient. In one embodiment, the method comprises providing a device according to the present invention. First, the bed attachment cable is attached to the bed frame. Next, the waist of the patient is encircled by the belt such that the belt attachment cable is between the patient's legs. Then, the belt attachment cable is connected to the harness attachment cable connector through the swivel, and through the harness attachment cable connector, if present. Finally, the patient reclines on the bed at a distance from the top end of the support to cause the tension provider to stretch, which transmits the tension through the harness attachment cable and harness, thereby placing traction on the lower vertebral column.

Figure 5:
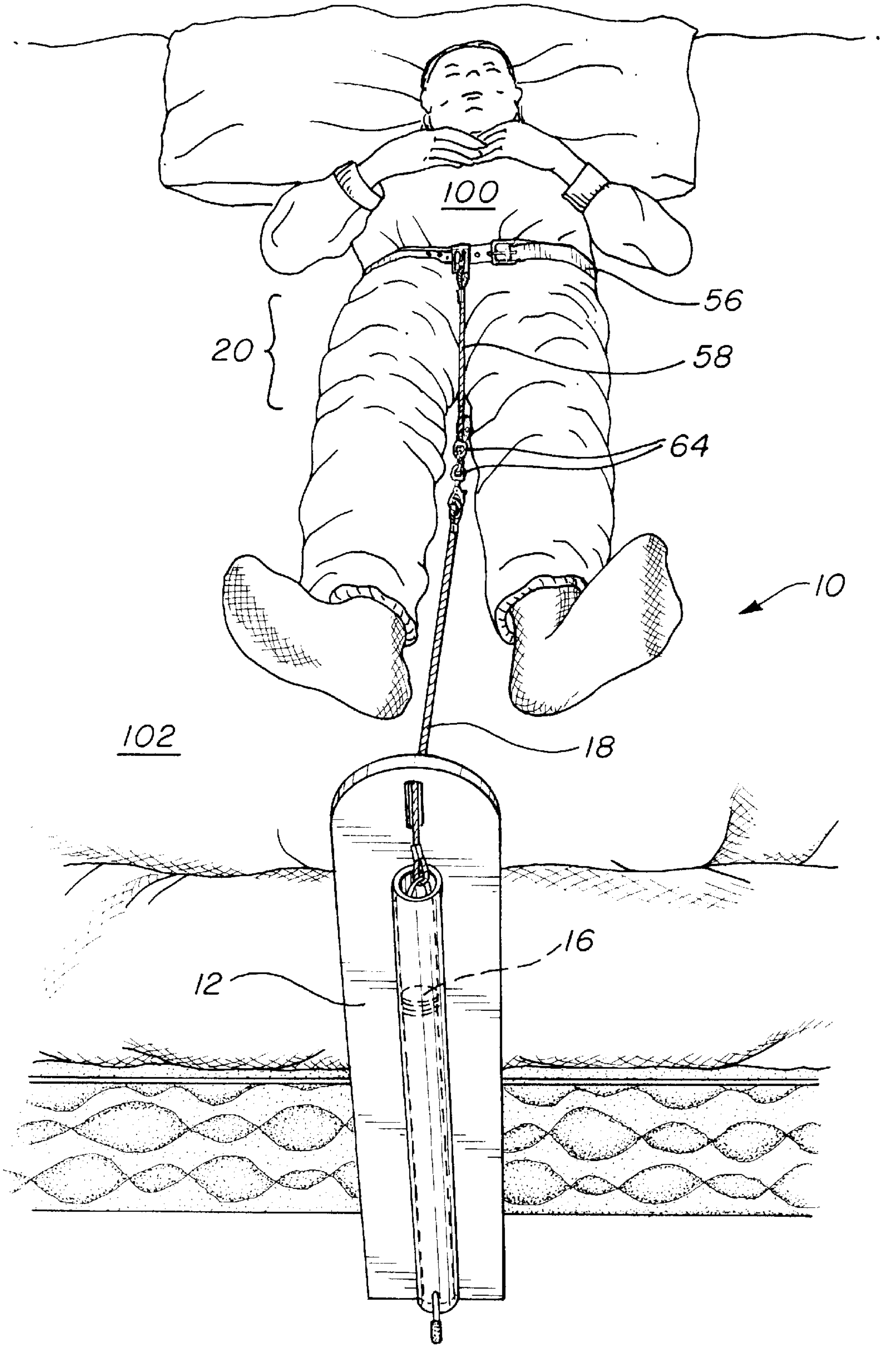
FIGS. 5–7 show top perspective views of a patient undergoing lower vertebral traction on a bed in a back reclining position, a lateral reclining position and a prone position, respectively.
Figure 6:
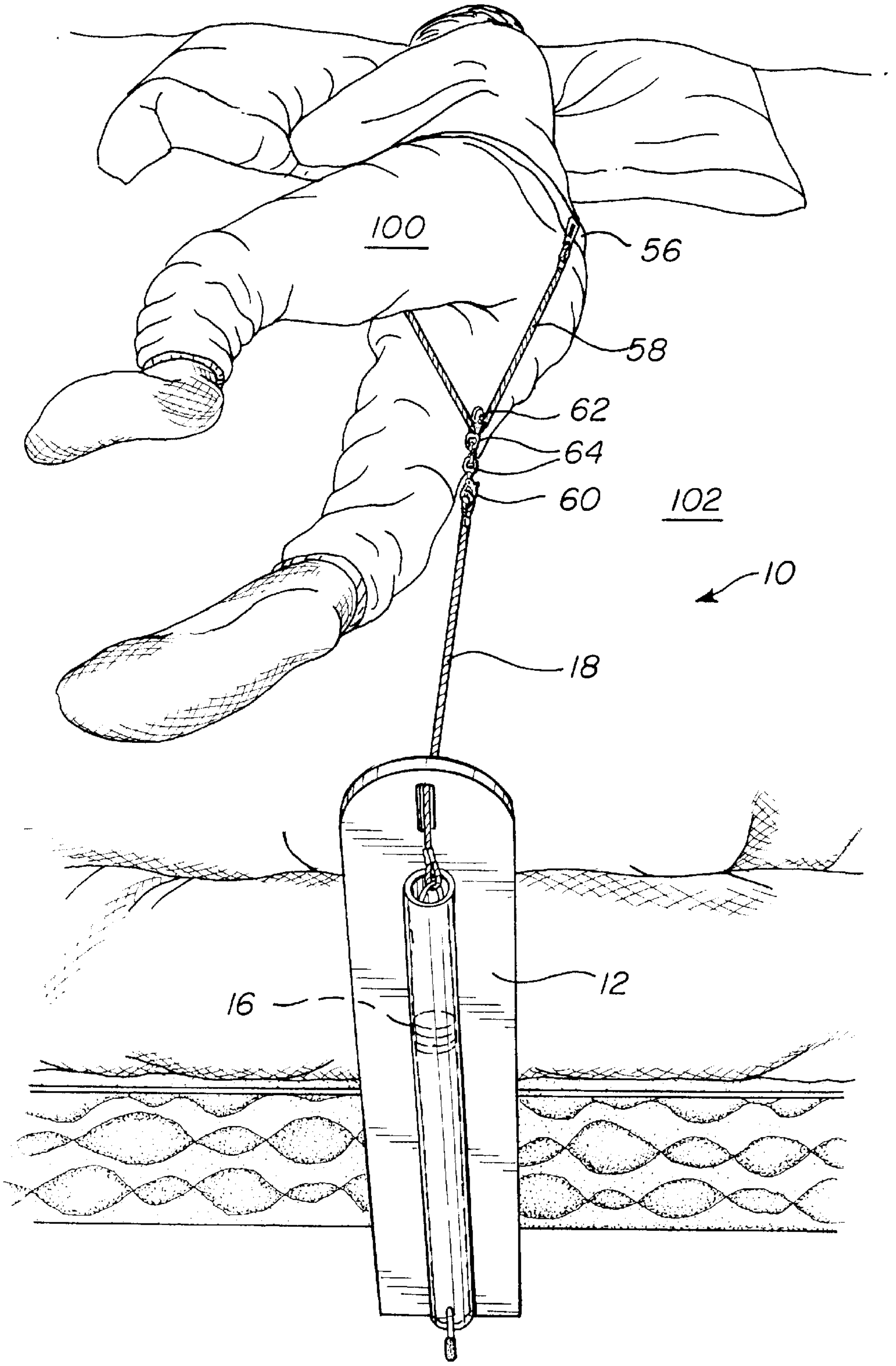
Figure 7:
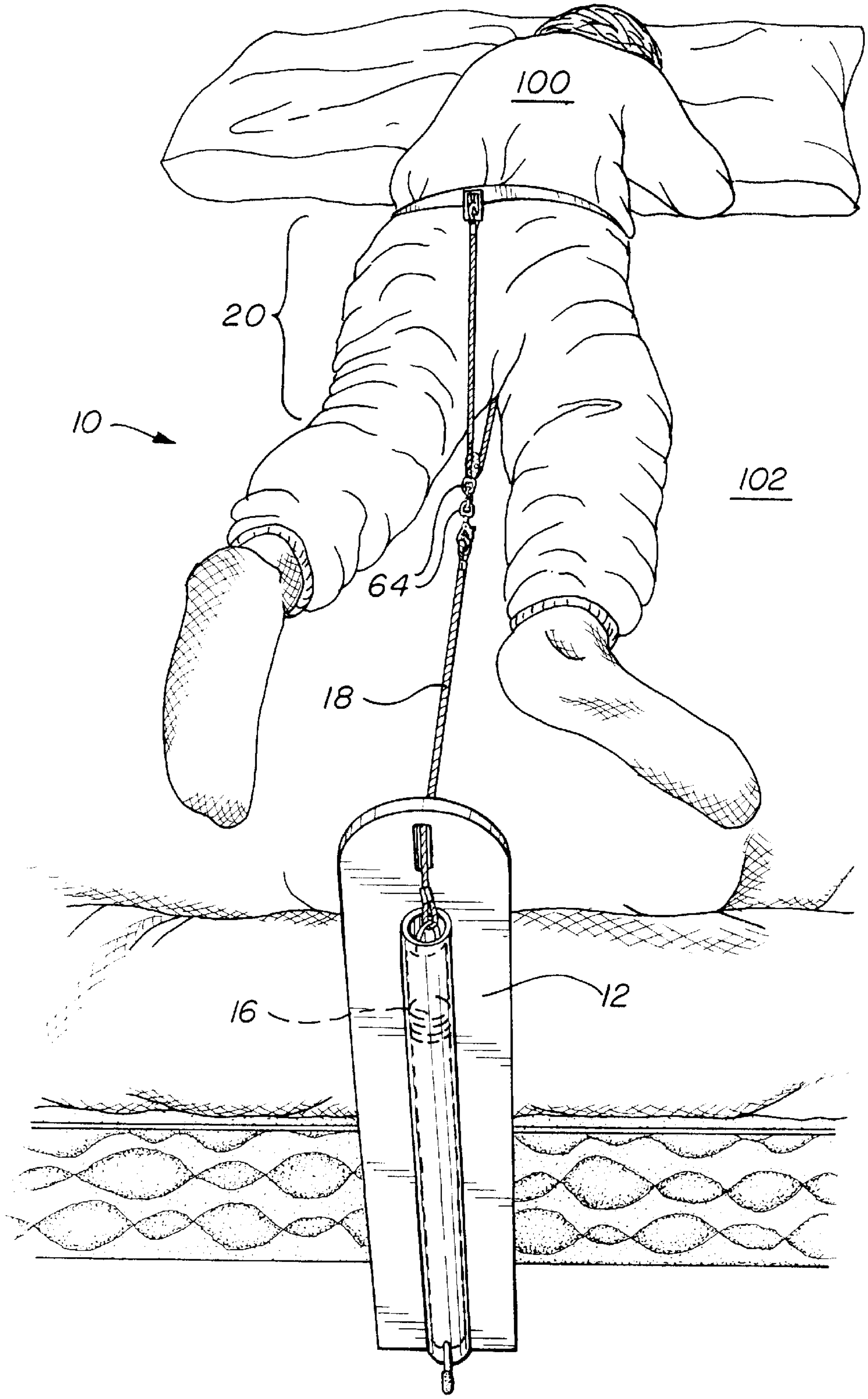

Referring now to FIGS. 5–7, there are shown top perspective views of a patient 100 undergoing lower vertebral traction on a bed 102 in a back reclining position, a lateral reclining position and a prone position, respectively, using a device 10 according to the present invention. As can be seen, traction is advantageously maintained on the lower vertebrae in all positions as the patient 100 rotates axially. Further advantageously, the patient 100 can disconnect the harness attachment cable 18 from the belt attachment cable 58 to leave the bed 102 while continuing to wear the harness 20. Then, when the patient 100 returns to the bed 102, traction can be easily reestablished by reconnecting the harness attachment cable 18 to the belt attachment cable 58 through the swivel 64.

In another embodiment, there is provided a method for applying traction to the lower vertebral column of a patient.

The method comprises placing a harness around a patient's waist where the harness is connected to a swivel and where placing the harness results in the swivel being between the patient's legs. Next, the swivel is attached to a tension provider at the foot of the bed and tension is allowed to transmit from the tension provider through the swivel between the patient's legs to the harness, thereby causing traction to the lower vertebral column of the patient.

Although the present invention has been discussed in considerable detail with reference to certain preferred embodiments, other embodiments are possible. Therefore, the scope of the appended claims should not be limited to the description of preferred embodiments contained in this disclosure.

I claim:

1. A vertebral traction device for applying traction to the lower vertebral column comprising:

a support having a top end, a bottom end, a front side and a back side;

a bed attachment cable having a proximal end and a distal end, where the proximal end of the bed attachment cable is attached to the support at or near the bottom end of the support;

a tension provider having a proximal end and a distal end, where the proximal end of the tension provider is attached to the support;

a harness attachment cable having a proximal end and a distal end, where the proximal end of the harness attachment cable is attached to the tension provider at or near the distal end of the tension provider, and where the distal end of the harness attachment cable has a long axis;

a harness comprising a belt and a belt attachment cable, where the belt attachment cable has a first end and a second end, and where the first end and the second end are connected to the belt;

a belt attachment cable connector slidably attached to the belt attachment cable; and a swivel connected to the belt attachment cable connector and to the harness attachment cable; and where the swivel allows the harness to rotate freely about the long axis of the distal end of the harness attachment cable.

2. The device according to claim 1, where the support comprises a board structure.

3. The device according to claim 2, where the top end of the support is rounded and smooth.

4. The device according to claim 2, where the bottom end of the support is flat.

5. The device according to claim 1, where the support comprises a foot member attached at or near the bottom end of the support.

6. The device according to claim 1, where the support comprises an enclosure connected to the back side for enclosing the tension provider.

7. The device according to claim 1, where the distal end of the bed attachment cable comprises a clip for reversibly attaching the distal end of the bed attachment cable to the bed attachment cable at a point proximal to the distal end of the bed attachment cable.

8. The device according to claim 1, where the tension provider is a spring.

9. The device according to claim 1, where the distal end of the harness attachment cable passes from the back side of the support to the front side of the support.

10. The device according to claim 1, additionally comprising a harness attachment cable connector, where the swivel is connected to the harness attachment cable by the harness attachment cable connector.

11. The device according to claim 1, where the belt attachment cable connector is attached to the belt attachment cable by a pulley.

12. A method for applying traction to the lower vertebral column of a patient reclining on a bed comprising:

a) providing a device according to claim 1;

b) attaching the bed attachment cable to the frame of the bed;

c) encircling the waist of the patient by the belt such that the belt attachment cable is between the patient's legs;

d) connecting the belt attachment cable to the harness attachment cable connector through the swivel; and e) positioning the patient on the bed at a distance from the top end of the support to cause the tension provider to stretch, thereby transmitting tension through the harness attachment cable and harness, and thereby placing traction on the lower vertebral column.

13. A method according to claim 12, where connecting the belt attachment cable to the harness attachment cable connector through the swivel further comprises attaching the swivel to a harness attachment cable connector connected to the harness attachment cable.

14. A vertebral traction device for applying traction to the lower vertebral column comprising:

a support having a top end, a bottom end, a front side and a back side;

a bed attachment cable having a proximal end and a distal end, where the proximal end of the bed attachment cable is attached to the support at or near the bottom end of the support;

a tension provider having a proximal end and a distal end, where the proximal end of the tension provider is attached to the support;

a harness attachment cable having a proximal end and a distal end, where the proximal end of the harness attachment cable is attached to the tension provider at or near the distal end of the tension provider, and where the distal end of the harness attachment cable has a long axis;

a harness comprising a belt and a belt attachment cable, where the belt attachment cable has a first end and a second end, and where the first end and the second end are connected to the belt; and a belt attachment cable connector slidably attached to the belt attachment cable by a pulley and attached to the harness attachment cable.

15. The device according to claim 14, where the support comprises a board structure.

16. The device according to claim 15, where the top end of the support is rounded and smooth.

17. The device according to claim 15, where the bottom end of the support is flat.

18. The device according to claim 14, where the support comprises a foot member attached at or near the bottom end of the support.

19. The device according to claim 14, where the support comprises an enclosure connected to the back side for enclosing the tension provider.

20. The device according to claim 14, where the distal end of the bed attachment cable comprises a clip for reversibly attaching the distal end of the bed attachment cable to the bed attachment cable at a point proximal to the distal end of the bed attachment cable.

21. The device according to claim 14, where the tension provider is a spring.

22. The device according to claim 14, where the distal end of the harness attachment cable passes from the back side of the support to the front side of the support.

23. The device according to claim 14, additionally comprising a swivel connected to the belt attachment cable connector and to the harness attachment cable, where the swivel allows the harness to rotate freely about the long axis of the distal end of the harness attachment cable.

24. The device according to claim 23, additionally comprising a harness attachment cable connector, where the swivel is connected to the harness attachment cable by the harness attachment cable connector.

25. A method for applying traction to the lower vertebral column of a patient reclining on a bed comprising:

a) providing a device according to claim 14;

b) attaching the bed attachment cable to the frame of the bed;

c) encircling the waist of the patient by the belt such that the belt attachment cable is between the patient's legs;

d) connecting the belt attachment cable to the harness attachment cable connector; and e) positioning the patient on the bed at a distance from the top end of the support to cause the tension provider to stretch, thereby transmitting tension through the harness attachment cable and harness, and thereby placing traction on the lower vertebral column.

* * * * *